(12) United States Patent
Parce

(10) Patent No.: US 6,233,048 B1
(45) Date of Patent: *May 15, 2001

(54) FOURIER DETECTION OF SPECIES MIGRATING IN A MICROCHANNEL

(75) Inventor: J Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/207,864

(22) Filed: Dec. 8, 1998

Related U.S. Application Data

(63) Continuation of application No. 08/941,679, filed on Sep. 30, 1997, now Pat. No. 5,852,495, which is a continuation of application No. 08/683,080, filed on Jul. 16, 1996, now Pat. No. 5,699,157.

(51) Int. Cl.[7] .................................................. G01B 21/00
(52) U.S. Cl. ........................................... 356/344; 73/61.48
(58) Field of Search ................................... 356/344, 318; 204/277 R, 182.8, 180.1; 250/461.2; 270/198.2, 198.3, 658, 656; 73/61.53, 23.39, 61.48

(56) References Cited

U.S. PATENT DOCUMENTS

| | | | |
|---|---|---|---|
| 2,850,940 | * | 9/1958 | Opperman ............................. 356/344 |
| 4,832,815 | * | 5/1989 | Kambara et al. ..................... 204/299 |
| 4,833,332 | * | 5/1989 | Robertson, Jr. et al. ............. 250/458 |
| 4,908,112 | * | 3/1990 | Pace ...................................... 204/299 |
| 5,104,508 | * | 4/1992 | Williams et al. ..................... 204/182 |
| 5,126,022 | * | 6/1992 | Soane et al. .......................... 204/180 |

(List continued on next page.)

OTHER PUBLICATIONS

Dasgupta et al., "Electroosmosis: A Reliable Fluid Propulsion System for Flow Injection Analysis,"*Anal Chem.* 66:1792–1798 (1994).
Jacobson et al., "Effects of Injection Schemes and Column Geometry on the Performance of Microchip Electrophoresis Devices," *Anal. Chem.* 66:1107–1113 (1994).
Jacobson et al., "High–Speed separations on a Microchip," *Anal. Chem.* 66:1114–1118. (1994).
Jacobson et al., "Open Channel Electrochromatography on a Microchip," *Anal. Chem.* 66:2369–2373 (1994).
Jacobson et al., "Precolumn Reactions with Electrophoretic Analysis Integrated on a Microchip," *Anal. Chem.* 66:4127–4131 (1994).
Jacobson et al., "Fused Quartz Substrates for Microchip Electrophoresis," *Anal. Chem.* 67:2059–2063 (1995).
Jacobson et al., "Microchip Electrophoresis with Sample Stacking," *Electrophoresis* 16:481–486 (1995).
Linhares et al., "Use of an On–Column Fracture in Capillary zone Electrophoresis for Sample Introduction, " 63:2076–2078 (1991).

(List continued on next page.)

*Primary Examiner*—Frank G. Font
*Assistant Examiner*—Michael P. Stafira
(74) *Attorney, Agent, or Firm*—Matthew B. Murphy; Gulshan H. Shaver

(57) ABSTRACT

The present invention provides a microfluidic system for fast, accurate and low cost electrophoretic analysis of materials in the fields of chemistry, biochemistry, biotechnology, molecular biology and numerous other fields. Light from periodically spaced regions along a channel in the microfluidic system are received by a photodetector. The intensity of light received by the photodetector is modulated by the movement of species bands through the channel under electrophoretic forces. By Fourier analysis, the velocity of each species band is determined and the identification of the species is made by its electrophoretic mobility in the channel.

15 Claims, 4 Drawing Sheets

U.S. PATENT DOCUMENTS

| | | | | |
|---|---|---|---|---|
| 5,162,654 | * | 11/1992 | Kostichka et al. | 250/458 |
| 5,213,673 | * | 5/1993 | Fujimiya et al. | 204/299 |
| 5,221,454 | * | 6/1993 | Manian et al. | 204/299 |
| 5,271,724 | * | 12/1993 | Van Lintel | 417/413 |
| 5,277,556 | * | 1/1994 | Van Lintel | 417/413 |
| 5,304,487 | * | 4/1994 | Wilding et al. | 435/291 |
| 5,324,401 | * | 6/1994 | Yeung et al. | 204/180 |
| 5,354,440 | * | 10/1994 | Allington | 204/180 |
| 5,376,252 | * | 12/1994 | Ekstrom et al. | 204/299 |
| 5,486,335 | * | 1/1996 | Wilding et al. | 422/55 |
| 5,498,392 | * | 3/1996 | Wilding et al. | 422/68.1 |
| 5,699,157 | | 12/1997 | Parce | 356/344 |

OTHER PUBLICATIONS

Manz et al., "Electroosmotic pumping and electrophoretic separations for miniaturized chemical analysis systems," *J. Micromech. Microeng.* 4:257–265 (1994).

Ramsey et al., "Microfabricated chemical measurement systems," *Nature Med.* 1:1093–1096 (1995).

Seiler et al., "Electroosmotic Pumping and Valveless control of FLuid Flow within a Manifold of Capillaries on a Glass Chip," *Anal. Chem.* 66:3485–3491 (1994).

* cited by examiner

FOURIER DETECTION OF SPECIES MIGRATING IN A MICROCHANNEL

CROSS-REFERENCE TO RELATED APPLICATIONS

This application is a continuation of U.S. patent application Ser. No. 08/941,679, filed Sep. 30, 1997, now U.S. Pat. No. 5,852,495 which is a continuation of U.S. patent application Ser. No. 08/683,080, filed Jul. 16, 1996 now U.S. Pat. No. 5,699,157.

BACKGROUND OF THE INVENTION

There has been a growing interest in the manufacture and use of microfluidic systems for the acquisition of chemical and biochemical information. Techniques commonly associated with the semiconductor electronics industry, such as photolithography, wet chemical etching, etc., are used in the fabrication of these microfluidic systems. The term, "microfluidic", refers to system or devices having channels and chambers are generally fabricated at the micron or submicron scale, e.g., having at least one cross-sectional dimension in the range of from about 0.1 $\mu$m to about 500 $\mu$m. Early discussions of the use of planar chip technology for the fabrication of microfluidic systems are provided in Manz et al., Trends in Anal. Chem. (1990) 10(5):144–149 and Manz et al., Adv. in Chromatog. (1993) 33:1–66, which describe the fabrication of such fluidic devices and particularly microcapillary devices, in silicon and glass substrates.

Application of microfluidic systems are myriad. For example, International Patent Appln. WO 96/04547, published Feb. 15, 1996, describes the use of microfluidic systems for capillary electrophoresis, liquid chromatography, flow injection analysis, and chemical reaction and synthesis. U.S. application Ser. No. 08/671,987, entitled "HIGH THROUGHPUT SCREENING ASSAY SYSTEMS IN MICROSCALE FLUIDIC DEVICES", filed Jun. 28, 1996 by J. Wallace Parce et al. and assigned to the present assignee, disclosed wide ranging applications of microfluidic systems in rapidly assaying compounds for their effects on chemical, and preferably, biochemical systems. The phase, "biochemical system," generally refers to a chemical interaction which involves molecules of the type generally found within living organisms. Such interactions include the full range of catabolic and anabolic reactions which occur in living systems including enzymatic, binding, signalling and other reactions. Biochemical systems of particular interest include, e.g., receptor-ligand interactions, enzyme-substrate interactions, cellular signalling pathways, transport reactions involving model barrier systems (e.g., cells or membrane fractions) for bioavailability screening, and a variety of other general systems.

As disclosed in International Patent Appln. WO 96/04547 and U.S. application Ser. No. 08/671,987 noted above, one of the operations which is suitable for microfluidic systems is capillary electrophoresis. In capillary electrophoresis charged molecular species, such as nucleic acids or proteins, for example, are separated in solution by an electric field. With very small capillary tubes as separation channels in a microfluidic system, resolution is enhanced because band broadening due to thermal convection is minimized. The requirement of only a small amount of sample material containing the molecular species is a further advantage of capillary electrophoresis in microfluidic systems.

Nonetheless, there is still room for improvement in capillary electrophoresis. One of the goals of microfluidic systems is high throughput. Presently capillary electrophoresis in microfluidic systems is performed by the observation of separating bands of species migrating in a separation channel under an electric field. The electrophoretic mobility of a species is determined by the time required from the entry of a test compound material into the separation channel for a species band from the test compound material to pass a detection point along the separation channel. The operation is completed after the last species band clears the detection point. See, for example, the above-cited International Patent Appln. WO 96/04547. While these operations are fast compared to macroscale electrophoretic methods, the operations fall short of a highly automated microfluidic system, such as disclosed in the above-mentioned U.S. application Ser. No. 08/671,987, for example.

In contrast, the present invention solves or substantially mitigates these problems. With the present invention, the electrophoretic mobility of each species is determined as the various species undergo electrophoresis in a microfluidic system. Identification of each species can be made automatically.

SUMMARY OF THE INVENTION

The present invention provides for a microfluidic system for high-speed electrophoretic analysis of subject materials for applications in the fields of chemistry, biochemistry, biotechnology, molecular biology and numerous other areas. The system has a channel in a substrate, a light source and a photoreceptor. The channel holds subject materials in solution in an electric field so that the materials move through the channel and separate into bands according to species. The light source excites fluorescent light in the species bands and the photoreceptor is arranged to receive the fluorescent light from the bands. The system further has a means for masking the channel so that the photoreceptor can receive the fluorescent light only at periodically spaced regions along the channel. The system also has an unit connected to analyze the modulation frequencies of light intensity received by the photoreceptor so that velocities of the bands along the channel are determined. This allows the materials to be analyzed.

In accordance with the present invention, the microfluidic system can also be arranged to operate with species bands which absorb the light from the light source. The absorbance of light by the species bands creates the modulation in light intensity which allow the velocities of the bands along the channel to be determined and the subject material to be analyzed.

The present invention also provides for a method of performing high-speed electrophoretic analysis of subject materials. The method comprises the steps of holding the subject materials in solution in a channel of a microfluidic system; subjecting the materials to an electric field so that the subject materials move through the channel and separate into species bands; directing light toward the channel; receiving light from periodically spaced regions along the channel simultaneously; and analyzing the frequencies of light intensity of the received light so that velocities of the bands along the channel can be determined for analysis of said materials. The determination of the velocity of a species band determines the electrophoretic mobility of the species and its identification.

DETAILED DESCRIPTION OF THE INVENTION

General Description of Microfluidic Systems

Figure 1:
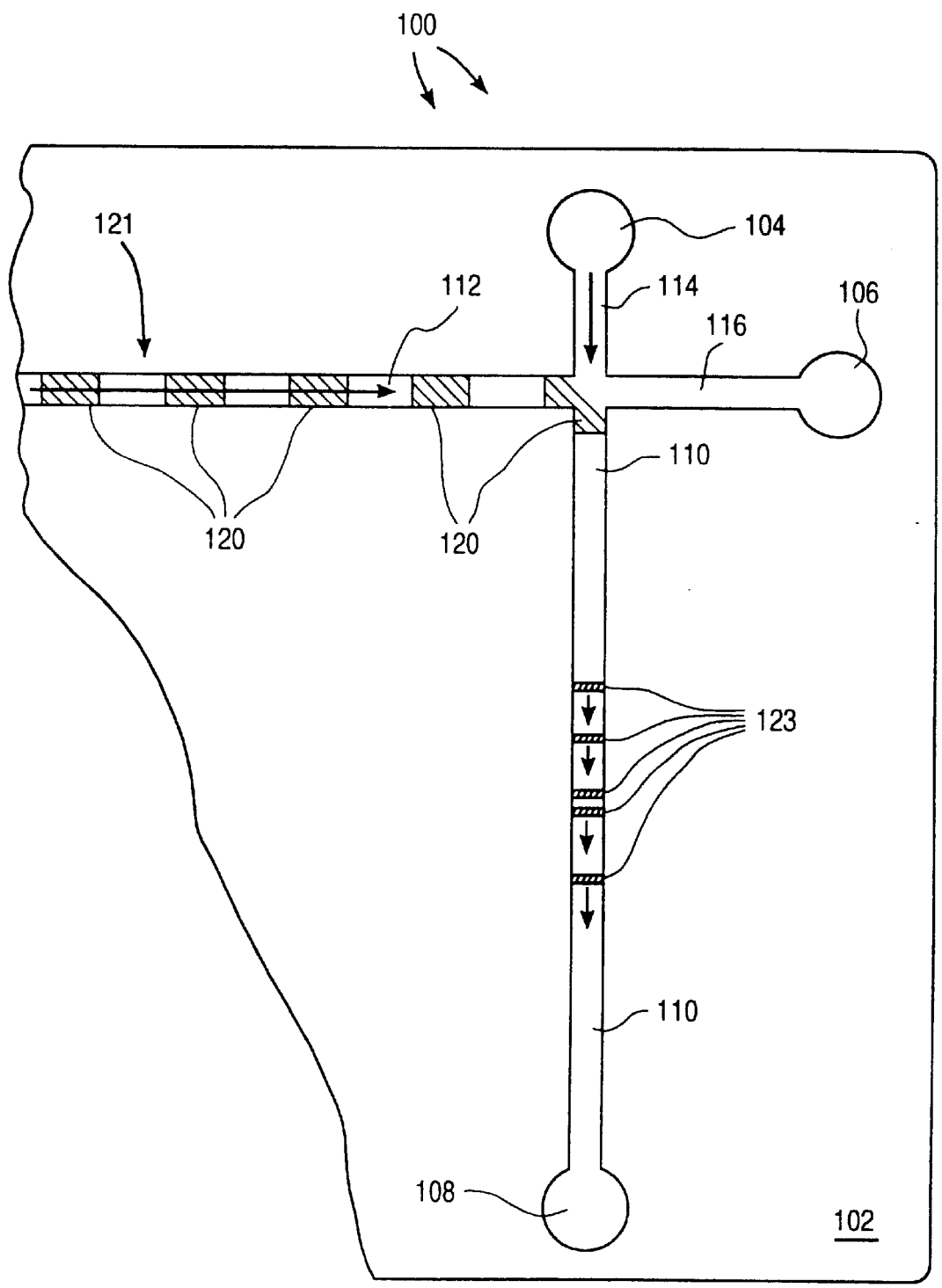
FIG. 1 is a schematic illustration of one embodiment of a microfluidic system.

FIG. 1 discloses a representative diagram of an exemplary microfluidic system 100 according to the present invention. As shown, the overall device 100 is fabricated in a planar substrate 102. Suitable substrate materials are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the system.

Useful substrate materials include, e.g., glass, quartz and silicon, as well as polymeric substrates, e.g., plastics. In the case of conductive or semiconductive substrates, there should be an insulating layer on the substrate. This is particularly important where the device incorporates electrical elements, e.g., electrical fluid direction systems, sensors and the like, or uses electroosmotic forces to move materials about the system, as discussed below. In the case of polymeric substrates, the substrate materials may be rigid, semi-rigid, or non-rigid, opaque, semi-opaque or transparent, depending upon the use for which they are intended. For example, devices which include an optical or visual detection element, are generally fabricated, at least in part, from transparent materials to allow, or at least, facilitate that detection. Alternatively, transparent windows of, e.g., glass or quartz, may be incorporated into the device for these types detection elements. Additionally, the polymeric materials may have linear or branched backbones, and may be crosslinked or non-crosslinked. Examples of particularly preferred polymeric materials include, e.g., polydimethysiloxanes (PDMS), polyurethane, polyvinylchloride (PVC) polystyrene, polysulfone, polycarbonate and the like.

The system shown in FIG. 1 includes a series of channels 110, 112, 114 and 116 fabricated into the surface of the substrate 102. As discussed in the definition of "microfluidic," these channels typically have very small cross sectional dimensions, preferably in the range from about 0.1 $\mu$m to about 100 $\mu$m. For the particular applications discussed below, channels with depths of about 10 $\mu$m and widths of about 60 $\mu$m work effectively, though deviations from these dimensions are also possible.

Manufacturing of these channels and other microscale elements into the surface of the substrate 102 may be carried out by any number of microfabrication techniques that are well known in the art. For example, lithographic techniques may be employed in fabricating glass, quartz or silicon substrates, for example, with methods well known in the semiconductor manufacturing industries. Photolithographic masking, plasma or wet etching and other semiconductor processing technologies define microscale elements in and on substrate surfaces. Alternatively, micromachining methods, such as laser drilling, micromilling and the like, may be employed. Similarly, for polymeric substrates, well known manufacturing techniques may also be used. These techniques include injection molding techniques or stamp molding methods where large numbers of substrates may be produced using, e.g., rolling stamps to produce large sheets of microscale substrates, or polymer microcasting techniques where the substrate is polymerized within a microfabricated mold.

Besides the substrate 102, the microfluidic system includes an additional planar element (not shown) which overlays the channeled substrate 102 to enclose and fluidly seal the various channels to form conduits. The planar cover element may be attached to the substrate by a variety of the means, including, e.g., thermal bonding, adhesives or, in the case of glass, or semi-rigid and non-rigid polymeric substrates, a natural adhesion between the two components. The planar cover element may additionally be provided with access ports and/or reservoirs for introducing the various fluid elements needed for a particular screen.

The system 100 shown in FIG. 1 also includes reservoirs 104, 106 and 108, which are disposed and fluidly connected at the ends of the channels 114, 116 and 110 respectively. As shown, sample channel 112, is used to introduce a plurality of different subject materials into the device. It should be noted that the term, "subject materials," simply refers to the material, such as a chemical or biological compound, of interest. Subject compounds may include a wide variety of different compounds, including chemical compounds, mixtures of chemical compounds, e.g., polysaccharides, small organic or inorganic molecules, biological macromolecules, e.g., peptides, proteins, nucleic acids, or extracts made from biological materials, such as bacteria, plants, fungi, or animal cells or tissues, naturally occurring or synthetic compositions.

Many methods have been described for the transport and direction of fluids, e.g., samples, analytes, buffers and reagents, within microfluidic systems or devices. One method moves fluids within microfabricated devices by mechanical micropumps and valves with in the device. See, published U.K. Patent Application No. 2 248 891 (Oct. 18, 1990), published European Patent Application No. 568 902 (May 2, 1992), U.S. Pat. Nos. 5,271,724 (Aug. 21, 1991) and 5,277,556 (Jul. 3, 1991). See also, U.S. Pat. No. 5,171,132 (Dec. 21, 1990) to Miyazaki et al. Another method uses acoustic energy to move fluid samples within devices by the effects of acoustic streaming. See, published PCT Application No. 94/05414 to Northrup and White. A straightforward method applies external pressure to move fluids within the device. See, e.g., the discussion in U.S. Pat. No. 5,304,487 to Wilding et al.

While these methods could be used to transfer the test compound materials to the separation channel for electrophoresis, a preferable method uses electric fields to move fluid materials through the channels of a microfluidic system. See, e.g., published European Patent Application No. 376 611 (Dec. 30, 1988) to Kovacs, Harrison et al., Anal. Chem. (1992) 64:1926–1932 and Manz et al. J. Chromatog. (1992) 593:253–258, U.S. Pat. No. 5,126,022 to Soane. Electrokinetic forces have the advantages of direct control, fast response and simplicity. Furthermore, the use of electrokinetic forces to move the subject materials about the channels of the microfluidic system 100 is consistent with the use of electrophoretic forces in the separation channel 110.

To provide such electrokinetic transport, the system 100 includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple independent voltage sources may be used. The voltage controller is electrically connected to each of the reservoirs via an electrode positioned or fabricated within each of the plurality of reservoirs. See, for example, published International Patent Application No. WO 96/04547 to Ramsey, which is incorporated herein by reference in its entirety for all purposes.

Alternatively, rather than voltage, another electrical parameter, such as current, may be used to control the flow of fluids through the channels. A description of such alternate electrical parametric control is found in U.S. application Ser. No. 08/678,436, entitled "VARIABLE CONTROL OF ELECTROOSMOTIC AND/OR ELECTROPHORETIC FORCES WITHIN A FLUID-CONTAINING STRUCTURE VIA ELECTRICAL FORCES", filed Jul. 3, 1996 by Calvin Y. H. Chow and J. Wallace Parce and assigned to the present assignee. This application is incorporated herein by reference in its entirety for all purposes.

Stated more precisely, electrokinetic forces may be separated into electroosmotic forces and electrophoretic forces. The fluid control systems used in the system of the present invention employ electroosmotic force to move, direct and mix fluids in the various channels and reaction chambers present on the surface of the substrate 102. In brief, when an appropriate fluid is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface possesses a net negative charge, whereas the fluid possesses an excess of protons or positive charge, particularly localized near the interface between the channel surface and the fluid.

By applying an electric field across the length of the channel, cations flow toward the negative electrode. Movement of the positively charged species in the fluid pulls the solvent with them. The steady state velocity of this fluid movement is generally given by the equation:

$$v = \frac{\epsilon \varepsilon E}{4\pi\eta}$$

where v is the solvent velocity, $\epsilon$ is the dielectric constant of the fluid, $\xi$ is the zeta potential of the surface, E is the electric field strength, and $\eta$ is the solvent viscosity. Thus, as can be easily seen from this equation, the solvent velocity is directly proportional to the zeta potential and the applied field.

Besides electroosmotic forces, there are also electrophoretic forces which affect charged molecules as they move through the system 100. In the transport of subject materials from one point to another point in the system 100, it is often desirable for the composition of the subject materials to remain unaffected in the transport, i.e., that the subject materials are not electrophoretically differentiated in the transport until desired. To do so, the subject materials are transported in fluid slug regions 120 of predetermined ionic concentrations. The regions are separated by buffer regions of varying ionic concentrations and represented by buffer regions 121 in FIG. 1. A related patent application, U.S. application Ser. No. 08/671,986, entitled "ELECTROPIPETTOR AND COMPENSATION MEANS FOR ELECTROPHORETIC BIAS," filed Jun. 28, 1996 by J. Wallace Parce and Michael R. Knapp, and assigned to the present assignee, explains various arrangements of slugs, and buffer regions of high and low ionic concentrations in transporting subject materials with electrokinetic forces. The application is incorporated herein by reference in its entirety for all purposes. The application also explains how the channel 112 may be fluidly connected to a source of large numbers of separate subject materials which are individually introduced into the sample channel 112 and subsequently into the separation channel 110 for analysis.

Electrophoresis in Microfluidic System and Operation

As described in the above-cited International Patent Appln. WO 96/04547 and the previously mentioned U.S. patent application Ser. No. 08/671,987, entitled "HIGH THROUGHPUT SCREENING ASSAY SYSTEMS IN MICROSCALE FLUIDIC DEVICES", the disclosures of which are incorporated herein by reference for all purposes. the slugs 120 of subject materials, separated by buffers 121, are moved through the sample channel 112 and into the separation channel 110. Each slug 120 is subjected to an electric field in the channel 110 so that the constituent species in each slug 120 separates into species bands 123, as shown in FIG. 1.

When the slugs 120 of subject materials are placed in the separation channel 110, the materials are subjected to an electric field by creating a large potential difference between the terminals in the reservoir 104 and 108. The species in the slugs separate according to their electric charges and sizes of their molecules. The species are subjected to electric fields in the range of 200 volts/cm. In accordance with one aspect of the present invention, the species are labeled with fluorescent label materials, such as fluorescent intercalating agents, such as ethidium bromide for polynucleotides, or fluorescein isothiocyanate or fluorescamine for proteins, as is typically done with conventional electrophoresis.

Figure 2A:
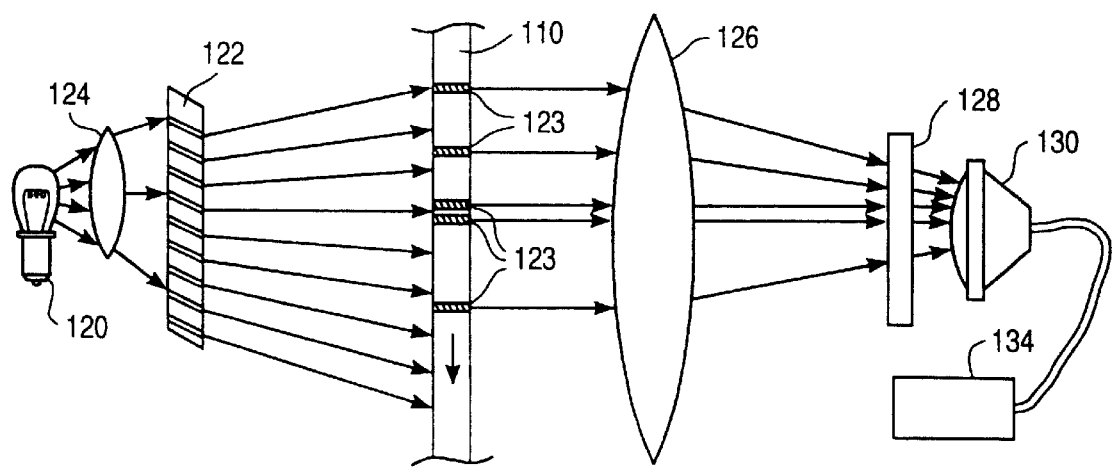
FIG. 2A is a representation of the details of a portion of the microfluidic system according to one embodiment of the present invention.

As shown in FIG. 2A, the arrangement has a light source 120, a first lens 124, a mask 122, the separation channel 110, a second lens 126, a filter 128, and a photoreceptor 130 connected to a frequency analyzer unit 134. The light source 120 emits light at wavelengths to energize the fluorescent labels of the species in the separation channel 110. Lamps, lasers and light-emitting diodes may be used for the source 120. The mask 122 is located between the light source 120 and the separation channel 110 and blocks light from reaching selected portions of the channel 110.

Figure 2B:
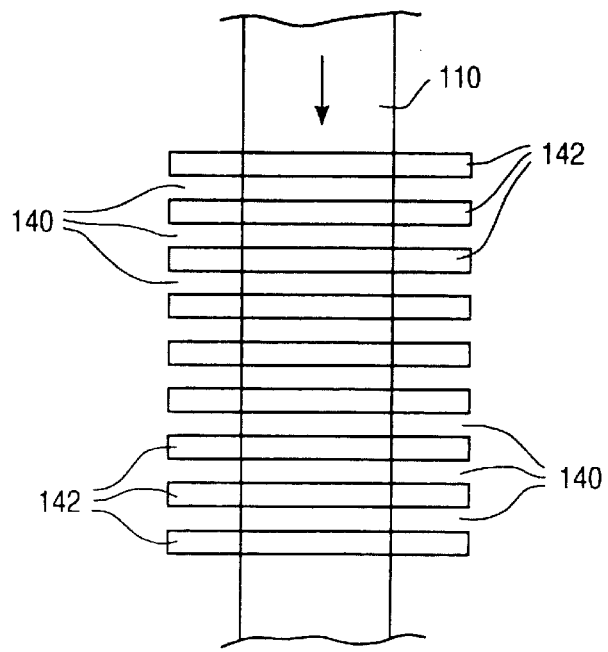
FIG. 2B is a detailed representation of a portion of the separation channel of microfluidic system of FIG. 2A.

The projection of the mask 122 by the light source 120 onto the separation channel 110 results in a series of alternating illuminated and darkened regions which are equally spaced along the channel 110. Each darkened region 140 has the same width as another darkened region along the separation channel 110 and is approximately the same width as the species bands 123 in the separation channel 110, as shown in FIG. 2B. The illuminated regions 142 along the separation channel 110 are also approximately the same width as the darkened regions 140. For example, with a separation column approximately 10 $\mu$m deep and 60 $\mu$m wide, the illuminated and darkened regions 142 and 140 are approximately 50–500 $\mu$m along the separation channel 110.

As each species band from the sample slugs travel through the alternating darkened and illuminated regions 140 and 142 respectively, the species bands 123 are alternately fluorescent in the illuminated regions 142 and unlit in the darkened regions 140. As each species travels down the separating channel 110, the species fluoresces off and on with a characteristic frequency corresponding to its velocity along the channel 110. The velocity, v, of the particular species is directly related to the electrophoretic mobility, $\mu_{ep}$, of that species:

$$v = \mu_{ep} * E$$

where E is the electric field. Thus a plurality of different species moving through the separation channel 110 fluoresces at a plurality of frequencies, each corresponding to a particular species.

The light from the separation channel 110 is focussed by the lens 126 upon the photoreceptor 130. The light received by the photoreceptor 130, which may be a photomultiplier tube, a photodiode, a CCD array, and the like, is converted into electrical signals which are, in turn, sent to the frequency analyzer unit 134. The frequency analyzer unit 134, by straightforward Fourier analysis, breaks the electrical signals into their component frequencies. These electrical signal frequencies are the same as that of the modulated light intensities generated by the species undergoing electrophoresis in the separation channel 110. The frequency of light intensity is related to the electrophoretic mobility of each species band. Hence, a computer unit with a calibrated look-up table can automatically identify each species according to its electrical signal frequency from the frequency analyzer unit 134. The electrophoresis operation is entirely automated.

Note that each species band 123 need not pass completely through the separation channel 110. Identification occurs as soon as a characteristic optical modulation frequency is generated after the species passes through a predetermined number of alternating darkened and illuminated regions in the channel 110. Thus electrophoresis is performed in a matter of seconds.

As stated above, the mask 122 is arranged such that the alternating darkened and illuminated regions are approximately the same width along the separation channel 110 with respect to each other and to the widest species band. This ensures the largest possible variation between the maxima and minima of light intensity from the fluorescent species bands passing through the mask regions.

As symbolically shown in FIG. 2A, the photoreceptor 130 is placed along an axis formed with the light source 120, the mask 122 and the lens 126. An alternative arrangement has the light source 120 and the mask 122 off the axis so that light from the source 120 directed toward the separation channel 110 is also directed away from the photoreceptor 130. This arrangement allows the photoreceptor 130 to be illuminated only by the fluorescent light from the labeled species in the channel 110. Furthermore, to avoid contamination of the optical signals received by the photoreceptor 130, a filter 128 may be used for the photoreceptor 130. The filter 128 is a band-pass filter transmitting light only at wavelengths emitted by the fluorescent species, and blocking light at other wavelengths, i.e., light from the source 120. Alternatively, the filter 128 might be selective toward blocking light at the light source wavelengths. Typically, the fluorescent label materials fluoresce at longer wavelengths than those of the source 120. For example, for polynucleotides labeled with ethidium bromide as subject materials for electrophoresis, a light source emitting light at 540 nm is used and the species bands fluoresce at 610 nm. For proteins labelled with fluorescein, a light source at 490 nm works with species bands fluorescing at 525 nm.

Figure 3A:
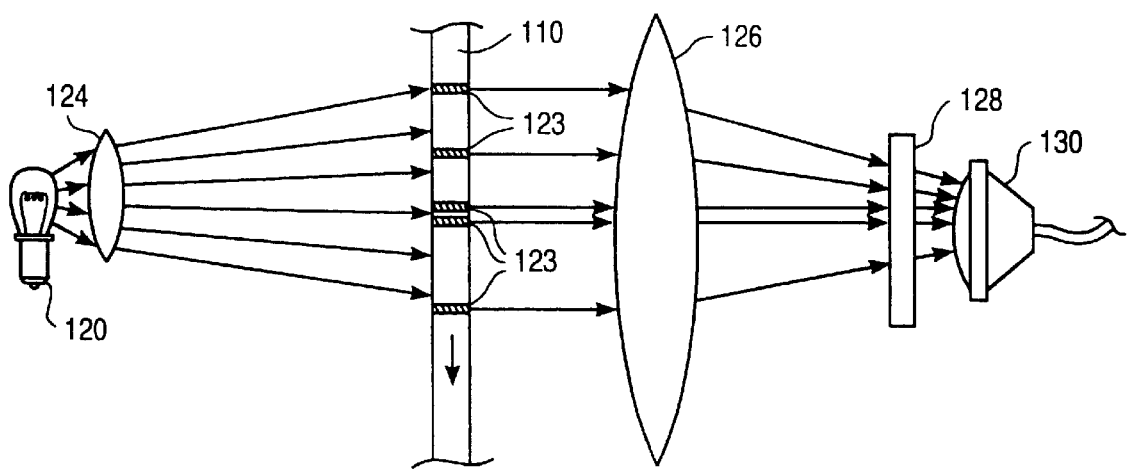
FIG. 3A represents an alternative arrangement of the portion of the microfluidic system according to another embodiment of the present invention.

As described above, the mask 122 is projected onto the separation channel 110. An alternative arrangement imposes the mask 122 onto the substrate itself so that a series of alternating darkened and light regions are created along the channel 110. Such an arrangement is illustrated in FIG. 3A.

Figure 3B:
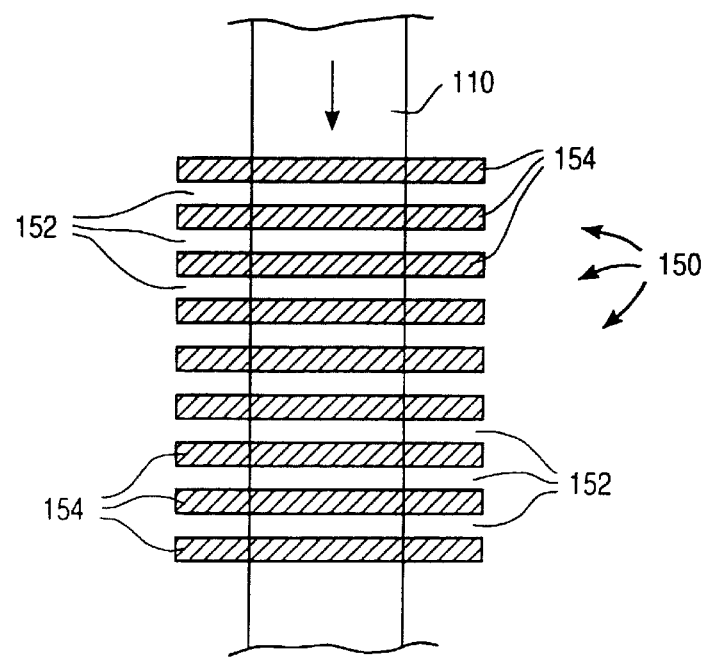
FIG. 3B is a detailed representation of a portion of the separation channel of microfluidic system of FIG. 3A.

The light source 120 illuminates the species bands 122 in the separation channel 110 directly. On the side of the channel 110 toward the photoreceptor 120, a mask 150 of alternating darkened and transparent regions 154 and 152 respectively are placed on the substrate 152, as shown in FIG. 3B. The dimensions and spacing of the regions 154 and 152 are the same as the projection of the mask 122 in FIGS. 2A and 2B.

Figure 4:
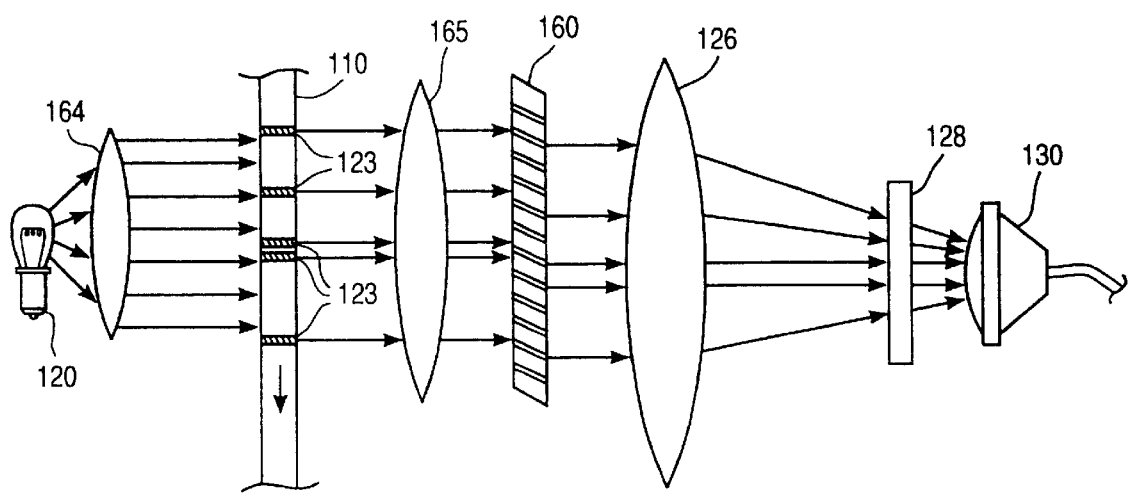
FIG. 4 represents still another arrangement of portion of the microfluidic system according to another embodiment of the present invention.

Still another arrangement projects the fluorescent species bands 123 in the separation channel 110 unto a mask 160, as shown in FIG. 4. After being collimated by a lens 164, light from the source 120 illuminates the species bands 123. Since light fluoresces from the bands 123 isotropically, the light is projected toward the mask 160 through a focussing lens 165. Light from the other side of the mask 160 is focused by the lens 126 onto the photodetector 120. As explained above, the elements of FIG. 4 illustrate a general relationship with each other. The lens 165, mask 160, lens 126, filter 128, and photoreceptor 130 need not be aligned with source 120, lens 164 and channel 110.

The arrangements above analyze the subject materials undergoing electrophoresis by the reception of fluorescent light from the moving species bands 123. The present invention also operates with the absorbance of light by the subject material. For example, using the arrangement of FIG. 2A, the light source 120 is selected to radiate light at wavelengths which are absorbed by the subject material. For proteins, the light source 120 may operate at wavelengths of 280 nm, for example. For polynucleotides, 260 nm is a suitable wavelength for the light source 120. The lens 126, filter 128 and photoreceptor are arranged to receive the light from the source 120 through the mask 122 and channel 120. The light source 120, lens 124, mask 122, channel 110, lens 126, filter 128 and photoreceptor 130 are optically aligned and the filter 128 is selected to pass light of the wavelength of interest from the source 120 to the photoreceptor 130. More typically for absorption measurements, the filter 128 is placed next to the source.

Rather than light from the species bands 123, darkness from the light-absorbing bands 123 moving in the channel 110 causes a varying signal to be received by the photoreceptor 130. Fourier analysis of the signal ultimately identifies the species in the channel 110. Similarly, the embodiments of the present invention illustrated in FIGS. 3A and 4 can be adapted to light absorbance by the species bands 123, rather than light fluorescence.

In another embodiment of the present invention, the mask 122 is eliminated. For example, a coherent light source, such as a laser, is used for the source 120 and a pair of slits are located between the source 120 and the channel 110. The slits are parallel to each other and perpendicular to the length of channel 110. By interference between the light emanating from the two slits, the light falls in intensities of alternating minima and maxima along the channel 110, like the operation of the mask 122 described previously. Light received from the periodically spaced locations of maxima allow the determination of the velocities of moving species bands 123 by the frequency analysis of the light intensity modulating in time, as described previously. This arrangement operates in either fluorescing or absorbing mode. Of course, other arrangements with one or more light sources 120 may also create light patterns of minima and maxima intensities along the channel 110 without a mask.

Speed and sensitivity of the present invention are much enhanced over previous systems which perform electrophoresis by the measurement of a species band past a detection point. The present invention has a higher signal-to-noise ratio since the light signals from the fluorescent bands 123 are averaged over time by the movement of the light signals past the mask regions, in contrast to a single observation at the detection point.

Of course, the present invention also has the other advantages of microfluidic systems, such as speed, low cost due to the low consumption of materials and the low use of skilled labor, and accuracy. The microfluidic system 100 has little or no contamination with high reproducibility of results.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of analyzing subject materials, comprising:
    transporting the subject materials through a microchannel and separating the subject materials into species bands;
    detecting the species bands at a plurality of periodically spaced regions along the microchannel; and
    analyzing frequencies at which the species bands are detected at the plurality of periodically spaced regions to determine a velocity of the species bands to analyze the subject materials.

2. The method of claim 1, wherein the subject materials comprise nucleic acids.

3. The method of claim 1, wherein the subject materials comprise proteins.

4. The method of claim 1, wherein the species bands comprise a fluorescent label, and the detecting step comprises exciting and detecting the fluorescent label.

5. The method of claim 1, wherein the detecting step comprises directing light at the periodically spaced regions and detecting a light signal from the microchannel.

6. The method of claim 1, wherein the detecting step comprises directing light at the microchannel and detecting a light signal from the plurality of periodically spaced regions.

7. The method of claim 1, wherein the analyzing step comprises analyzing the frequencies by Fourier analysis to determine the velocities of the species bands.

8. The method of claim 1, wherein the transporting step comprises electrophoretically transporting the subject materials through the microchannel.

9. The method of claim 1, wherein the microchannel disposed in a planar substrate.

10. A microfluidic system, comprising:
    a microchannel configured to separate a subject material into species bands;
    a detection system for detecting the species bands at a plurality of periodically spaced regions along the microchannel;
    a frequency analyzer unit operably linked to the detection system for monitoring a frequency at which the species bands past the plurality of periodically spaced regions as detected by the detection system, and determining a velocity of the species bands based upon the frequency.

11. The microfluidic system of claim 10, wherein the microchannel comprises a channel disposed with a planar substrate.

12. The microfluidic system of claim 10, wherein the microchannel intersects at least a second microchannel disposed in the planar substrate.

13. The microfluidic system of claim 10, wherein the substrate is selected from glass and polymer substrates.

14. The microfluidic system of claim 10, wherein the microchannel comprises at least one cross-sectional dimension between about 0.1 and 100 $\mu$m.

15. The microfluidic system of claim 12, wherein the planar substrate comprises at least first and second planar substrate layers, the microchannel being disposed in a first surface of the first planar substrate, and the second substrate overlaying the first substrate to enclose and fluidly seal the microchannel.

* * * * *

UNITED STATES PATENT AND TRADEMARK OFFICE
CERTIFICATE OF CORRECTION

PATENT NO. : 6,233,048 B1
DATED : May 15, 2001
INVENTOR(S) : Parce

It is certified that error appears in the above-identified patent and that said Letters Patent is hereby corrected as shown below:

Column 10,
Line 7, after "microchannel" please insert -- is --.
Line 22, please delete "with" and insert -- within --.

Signed and Sealed this

Twenty-seventh Day of November, 2001

Attest:

NICHOLAS P. GODICI
*Acting Director of the United States Patent and Trademark Office*

*Attesting Officer*